(12) United States Patent
de Kruijf et al.

(10) Patent No.: US 10,857,314 B2
(45) Date of Patent: Dec. 8, 2020

(54) MOUTHPIECE AND INHALER

(71) Applicant: SHL MEDICAL AG, Zug (CH)

(72) Inventors: Wilhelmus P. J. de Kruijf, Enschede (NL); Jeroen M. Wissink, Enschede (NL); Marcus Söderlund, Stockholm (SE); Nils Ronquist, Stockholm (SE); Johan Egerström, Saltsjö-Boo (SE)

(73) Assignee: SHL MEDICAL AG, Zug (CH)

( * ) Notice: Subject to any disclaimer, the term of this patent is extended or adjusted under 35 U.S.C. 154(b) by 338 days.

(21) Appl. No.: 15/033,406

(22) PCT Filed: Oct. 29, 2014

(86) PCT No.: PCT/EP2014/073206
§ 371 (c)(1),
(2) Date: Apr. 29, 2016

(87) PCT Pub. No.: WO2015/063144
PCT Pub. Date: May 7, 2015

(65) Prior Publication Data
US 2016/0279354 A1    Sep. 29, 2016
US 2019/0117912 A9    Apr. 25, 2019

Related U.S. Application Data

(60) Provisional application No. 61/900,140, filed on Nov. 5, 2013.

(30) Foreign Application Priority Data

Nov. 1, 2013  (SE) ..................... 1351297

(51) Int. Cl.
*A61M 15/00*    (2006.01)

(52) U.S. Cl.
CPC .... *A61M 15/0021* (2014.02); *A61M 15/0086* (2013.01); *A61M 2205/586* (2013.01)

(58) Field of Classification Search
None
See application file for complete search history.

(56) References Cited

U.S. PATENT DOCUMENTS 3,998,226 A    12/1976  Harris
4,535,765 A *  8/1985  Paoluccio ......... A61M 16/0048
                                             128/203.11

(Continued)

FOREIGN PATENT DOCUMENTS

GB        2454742 A       5/2009
WO    2010/073148 A1      7/2010
WO    2011/095762 A1      8/2011

OTHER PUBLICATIONS

EPO, Int'l Search Report in PCT/EP2014/073206, dated Mar. 11, 2015.

*Primary Examiner* — Rachel T Sippel
(74) *Attorney, Agent, or Firm* — McDonnell Boehnen Hulbert & Berghoff LLP

(57) ABSTRACT

A mouthpiece for a handheld inhaler is disclosed. A housing of the mouthpiece includes an inlet, an outlet opening, and a channel extending through the housing connecting the inlet and the outlet opening for directing an aerosol from the inlet to the outlet opening. An anterior portion of the housing (4) is configured for placement in the mouth of a patient. The anterior portion of the housing is configured to direct the outlet opening upwardly in the patient's oral cavity when in the mouth of the patient. Other embodiments include an outlet opening placed closer to the upper side of the housing than to the lower side of the housing. Further, an inhaler having a mouthpiece is disclosed.

14 Claims, 4 Drawing Sheets

(56) References Cited

U.S. PATENT DOCUMENTS

| | | | | |
|---|---|---|---|---|
| 5,012,804 | A | * | 5/1991 | Foley ................ A61M 15/0086 128/200.14 |
| 5,575,280 | A | * | 11/1996 | Gupte ............... A61M 15/0065 128/203.15 |
| 5,746,197 | A | | 5/1998 | Williams |
| 6,412,481 | B1 | | 7/2002 | Bienvenu et al. |
| 6,779,521 | B1 | * | 8/2004 | Schmehl ................ A61M 11/06 128/200.18 |
| 2005/0005933 | A1 | * | 1/2005 | Seppala ............ A61M 15/0065 128/203.15 |
| 2007/0062520 | A1 | * | 3/2007 | Nobutani .......... A61M 15/0085 128/200.14 |
| 2009/0050137 | A1 | * | 2/2009 | Wissink ................ A61M 11/06 128/200.14 |
| 2012/0240922 | A1 | | 9/2012 | Denyer et al. |
| 2013/0081617 | A1 | * | 4/2013 | Cavendish ........ A61M 16/0816 128/203.12 |
| 2013/0267864 | A1 | | 10/2013 | Addington et al. |
| 2013/0319407 | A1 | * | 12/2013 | Liu ...................... A61M 15/06 128/202.21 |
| 2015/0283338 | A1 | * | 10/2015 | Colosio ............. A61M 15/0028 128/203.15 |

\* cited by examiner

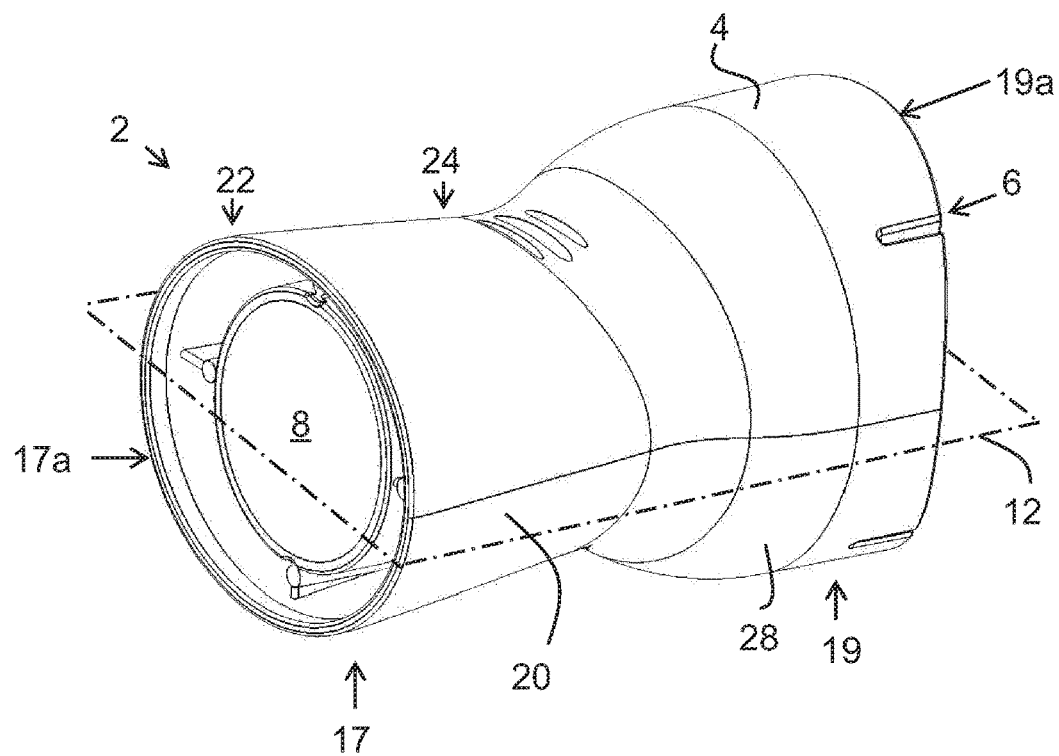
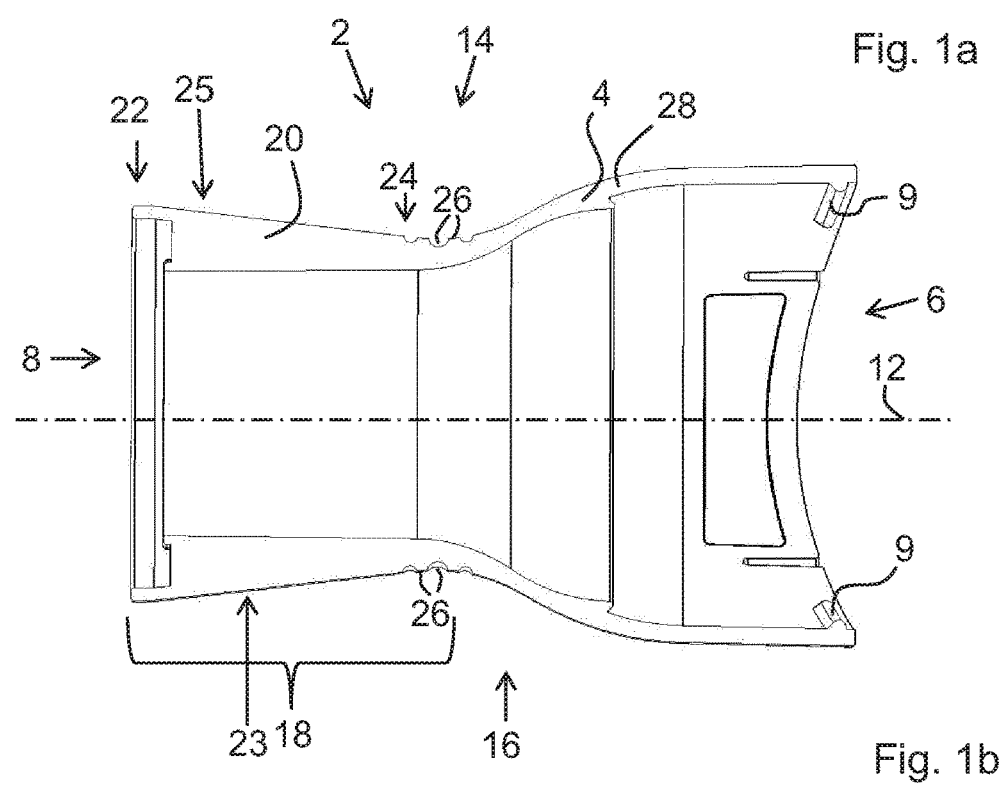
Fig. 1a
Fig. 1b

MOUTHPIECE AND INHALER

TECHNICAL FIELD

Embodiments disclosed herein relate to mouthpieces for inhalers for inhaling a medicament in aerosol form. Other embodiments herein relate to inhalers for inhaling a medicament in aerosol form.

BACKGROUND

Medicament administration via inhalation from a handheld inhaler is a well-known way of medicament administration to a patient. Some medicaments may be administered in powder form other medicament may be in liquid form which are administered as small droplets, both medicament forms may be referred to as aerosols. A patient puts a mouthpiece of the inhaler into his or her mouth and ejects a medicament dose, which is inhaled into the lungs of the patient.

Naturally, it is desirable that as much as possible of the medicament dose reaches the lungs of the patient. If the mouthpiece is directed towards the tongue or the teeth of the patient, an unnecessary large part of the medicament dose remain in the mouth of the patient and will not reach the lungs of the patient.

EP2381991 discloses an apparatus comprising a stepped mouthpiece for aerosol drug delivery. The apparatus aids in administering inhaled pharmaceutical aerosol to a patient. The apparatus is used in conjunction with an aerosol delivery device. The mouthpiece comprises steps on the top and bottom of the apparatus, which when used aid the patient in causing mandibular advancement, and opening of the mouth, also causing opening of the patient's airway, resulting in improved aerosol lung deposition. The steps are displaced horizontally in relation to each other when the mouthpiece is inserted into the mouth of a patient. The patient biting on the two steps causes the mandibular advancement.

There is a need for alternative solutions, of administering a medicament in aerosol form to the lungs of a patient.

SUMMARY

It is an object to provide a mouthpiece which improves the administering of a medicament in aerosol form to the lungs of a patient.

According to an aspect, this object is achieved by a mouthpiece for use with a handheld inhaler, the mouthpiece comprising a housing, wherein the housing comprises:

an inlet connectable to a medicament delivery device comprising a medicament container delivering an aerosol, an outlet opening for the aerosol, and a channel extending through the housing connecting the inlet and the outlet opening for directing the aerosol from the inlet to the outlet opening, wherein a plane extends through and along the channel, the plane defining on respective sides thereof an upper side and a lower side of the housing. An anterior portion of the housing is adapted to be placed in a mouth of a patient. The anterior portion of the housing is configured to direct the outlet opening upwardly in the oral cavity when the anterior portion is placed in the mouth of the patient.

Since the outlet opening is upwardly directed in the mouth of the patient, an aerosol from the inhaler being ejected into the mouth of the patient from the outlet opening of the mouthpiece is directed along the tongue of the patient, rather than towards the tongue. The aerosol will thus largely avoid sticking to the tongue and instead follow the oral cavity to the pharynx, the tracheal and the lungs of the patient. As a result, the above mentioned object is achieved.

It has been realized by the inventors that the mouthpiece as such may be configured to aid the patient in positioning the anterior portion in a mouth of a patient in a manner to improve the administering of an aerosol from an inhaler to the lungs of a patient.

In use, when the mouthpiece forms part of an inhaler, the plane may be upwardly inclined when the anterior portion is inserted into the mouth of the patient. Some medicaments may be administered in powder form other medicament may be in liquid form which are administered as small droplets, approximately 1-9 μm in diameter. Herein both medicament forms will be referred to as aerosols. A patient puts the anterior portion of the mouthpiece of the inhaler into his, or her, mouth and ejects via the outlet opening a medicament dose, which is inhaled into the lungs of the patient.

According to embodiments, the anterior portion of the housing may comprise a frusto-conical portion, the frusto-conical portion comprising a base extending substantially perpendicularly to the plane and a top extending substantially perpendicularly to the plane. The outlet opening may be arranged in the base, and the channel may extend through the top, between the inlet and the outlet opening. Accordingly, when placed in the mouth of the patient the wider base will be positioned farther into the oral cavity than the narrower top. Thus, a first portion of the outer surface of the frusto-conical portion may abut against the tongue, and a second portion of the outer surface may abut against the palate behind the front teeth. Due the nature of the frusto-conical shape and the outlet opening being arranged in the base, the outlet opening will be directed upwardly into the oral cavity of the patient when abutting against the tongue and the palate directing an aerosol into the middle of the oral cavity. The smaller size at the top than at the base will encourage a patient to place his, or her, lips around the top of the frusto-conical portion. Thus, it may be ensured that the outlet opening is positioned sufficiently far into a mouth of the patient.

According to embodiments, the outlet opening may be smaller than the base of the frusto-conical portion, and the outlet opening may be centred in the base of the frusto-conical portion. In this manner, at the outlet opening, a distance may be created between the outlet opening and the tongue and a distance may be created between the outlet opening and the palate. Thus, the aerosol will be directed into the middle of the oral cavity.

According to embodiments, the base of the frusto-conical portion may be oval. In this manner the anterior portion may be positioned centrally in the oral cavity, seen in a lateral direction.

According to embodiments, an outer surface of the housing at the top of the frusto-conical portion may be provided with indentations and/or protrusions. In this manner a patient may sense the indentations and/or protrusions with his, or her, tongue, teeth, or lips to ensure that the entire anterior portion has been placed in the mouth of the patient. In particular, a patient may be instructed to sense the indentations and/or protrusions with the tip of his, or her, tongue. Thus, the tongue will be positioned out of the way of the outlet opening. Moreover, the mouthpiece will be angel away from the tongue.

According to embodiments, groove portions adapted for placing lips of a patient there against may extend at least partially around the housing adjacent to the anterior portion.

At least one groove portion on the upper side may extends closer to the outlet opening than at least one groove portion on the lower side. In this manner, when the patient places his or her lips in the groove portions on the upper side and on the lower side, the anterior portion will be placed in the mouth of the patient at an angle with the plane upwardly inclined to direct the outlet opening upwardly in the oral cavity.

According to embodiments, the groove portions may comprise convexly concavely curved bottom surfaces. In this manner the groove portions are adapted for placing the lips of the patient there against.

According to a further aspect, the above mentioned object is achieved by a mouthpiece for use with a handheld inhaler, the mouthpiece comprising a housing, wherein the housing comprises:

an inlet connectable to a medicament delivery device comprising a medicament container delivering an aerosol, an outlet opening for the aerosol, and a channel extending through the housing connecting the inlet and the outlet opening for directing the aerosol from the inlet to the outlet opening, wherein a plane extends through and along the channel, the plane defining on respective sides thereof an upper side of the housing and a lower side of the housing. An anterior portion of the housing is adapted to be placed in a mouth of a patient. The outlet opening is placed closer to the upper side of the housing than to the lower side of the housing.

Since the outlet opening is placed closer to the upper side of the housing than to the lower side of the housing, an aerosol from the inhaler being directed into the mouth of the patient from the outlet opening of the mouthpiece is directed over the tongue of the patient, rather than towards the tongue. The aerosol will thus largely avoid sticking to the tongue and instead follow the oral cavity to the pharynx, the tracheal, and the lungs of the patient. As a result, the above mentioned object is achieved.

Also this aspect follows the line of thought along which the inventors have realized that the mouthpiece as such may be configured to aid the patient in placing the anterior portion in a mouth of a patient in a manner to improve the administering of an aerosol from an inhaler to the lungs of a patient.

According to embodiments, a channel-forming wall element of the channel may form at least a portion of an upper surface of the anterior portion on the upper side of the housing. A distance element positioned a distance from the channel may form at least a portion of a lower surface of the anterior portion on the lower side of the housing. In this manner the outlet opening may be placed closer to the upper side of the housing than to the lower side of the housing to create a distance between the tongue and the outlet opening.

According to embodiments, the mouthpiece may comprise a front surface extending substantially perpendicularly to the plane, wherein the outlet opening is arranged in the front surface.

According to a further aspect there is provided an inhaler comprising a mouthpiece according to any aspect or embodiment disclosed herein. The inhaler may be a handheld inhaler.

Further features and advantages will become apparent when studying the appended claims and the following detailed description.

BRIEF DESCRIPTION OF THE DRAWINGS

Various aspects of embodiments, including their particular features and advantages, will be readily understood from the example embodiments discussed in the following detailed description and the accompanying drawings, in which:

FIGS. 1a-4 illustrate various embodiments of mouthpieces for use with handheld inhalers.

DETAILED DESCRIPTION

Figure 2A:
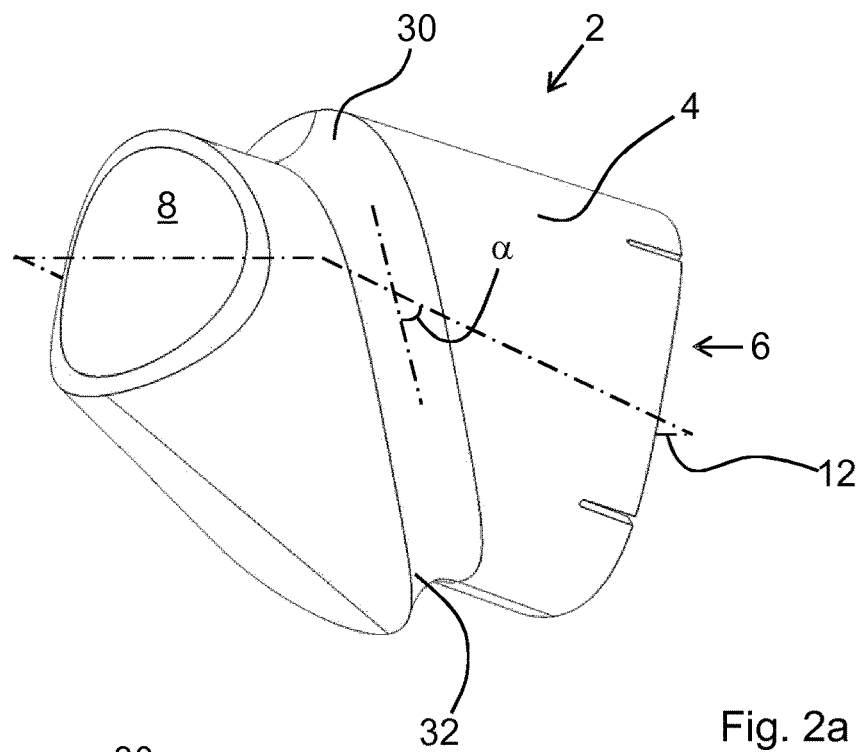

Aspects of example embodiments will now be described more fully. Like numbers refer to like elements throughout. Well-known functions or constructions will not necessarily be described in detail for brevity and/or clarity.

FIGS. 1a and 1b illustrate embodiments of a mouthpiece 2 for use with a handheld inhaler. The mouthpiece 2 forms a part of the inhaler, which is arranged to conduct an aerosol from a medicament container of the inhaler into an oral cavity of a patient. The mouthpiece 2 comprises a housing 4. The housing 4 comprises an inlet 6 and an outlet opening 8. The inlet 6 is connectable to a medicament delivery device of the inhaler comprising the medicament container delivering the aerosol. The mouthpiece 2 may for instance be connected to a body of an inhaler by means of a snap-fit connection, protrusions 9 of which are shown in FIG. 1b. Through the outlet opening 8 the aerosol is adapted to be administered into the oral cavity to be inhaled into the lungs of the patient. A channel 10 extends through the housing 4 and connects the inlet 6 and the outlet opening 8. Thus, the channel 10 is adapted to direct the aerosol from the inlet 6 to the outlet opening. A plane 12 extends through and along the channel 10. The plane 12 defines on respective sides thereof an upper side 14 of the housing 4 and a lower side 16 of the housing 4. The outlet opening 8 is arranged at a first end portion 17 of the housing 4, between the upper side 14 and the lower side 16. The inlet 6 is arranged at a second end portion 19 of the housing 4, between the upper side 14 and the lower side 16. When the mouthpiece 2 is positioned to be placed in the mouth of the patient, the upper side 14 is arranged to face substantially upwardly and the lower side 16 is arranged to face substantially downwardly.

An anterior portion 18 of the housing 4 is adapted to be placed in the mouth of the patient. The anterior portion 18 of the housing 4 is configured to direct the outlet opening 8 upwardly in the oral cavity when the anterior portion 18 is placed in the mouth of the patient. The anterior portion 18 further has an anterior end face 18a and the second end portion 19 has a posterior end face 19a.

In these embodiments, the anterior portion 18 of the housing 4 comprises a frusto-conical portion 20. The frusto-conical portion 20 comprises a base 22 extending substantially perpendicularly to the plane 12 and a top 24 extending substantially perpendicularly to the plane 12. The outlet opening 8 is arranged in the base 22. The channel 10 extends through the top 24, between the inlet 6 and the outlet opening 8.

Seen in a direction from the base 22 towards the top 24 along the plane 12, a wide housing portion 28 is arranged adjacent to the top 24. The anterior portion 18 thus, is terminated by the wide housing portion 28.

In a frusto-conical shape the base 22 is wider than the top 24. When placed in the mouth of the patient, the wide base 22 of the frusto-conical portion 20 will be positioned farther into the oral cavity than the narrow top 24. The patient places his or her lips around the top 24. A first portion of an outer surface of the frusto-conical portion 20 on the lower side 16 of the housing 4 will abut against the tongue of the patient. A second portion of the outer surface of the frusto-conical portion 20 on the upper side 14 of the housing 4 may abut against the palate behind the front teeth of the patient. Thus, the natural shape of the mouth cavity and the tongue of the patient will position the frusto-conical portion 20 with the plane 12 upwardly inclined, e.g. at an angle of 30-60 degrees to a vertical axis in the mouth of the patient. Accordingly, the outlet opening 8, being arranged in the base 22, will be directed upwardly into the oral cavity of the patient. The aerosol from the medicament delivery device will thus be administered into a middle portion of the oral cavity between the tongue and the palate. Thus, minimising the aerosol deposition on the tongue and/or the palate, helping the aerosol to reach the lungs of the patient.

The outlet opening 8 is smaller than the base 22 of the frusto-conical portion 20. The outlet opening 8 is centred in the base 22 of the frusto-conical portion. The distances created between the tongue and the outlet opening 8 and the distance created between the palate and the outlet opening 8 by the outlet opening 8 being smaller than the base 22 also aids in administering the aerosol in the middle portion of the oral cavity. Thus, minimising the aerosol deposition on the tongue and/or the palate, helping the aerosol to reach the lungs of the patient.

The base 22 of the frusto-conical portion 20 is oval. An outer surface of the housing 4 at the top 24 of the frusto-conical portion 20 is provided with indentations and/or protrusions 26. A patient may sense the indentations and/or protrusions 26 with his or her tongue, teeth, or lips to ensure that the entire anterior portion 18 has been placed in the mouth.

The following dimensions are mentioned purely as an example. The mouthpiece 2 may have a length of 10-70 mm. The length of the anterior portion 18 may be 10-40 mm. The large diameter of the base 22 may be 25-40 mm and the small diameter of the base 22 may be 15-25 mm. The large diameter of the top 24 may be 20-30 mm and the small diameter of the top 24 may be 12-20 mm. The diameter of the wide portion 28 may be 15-35 mm. The diameter of the outlet opening 8 may be 14-25 mm.

Figure 2B:
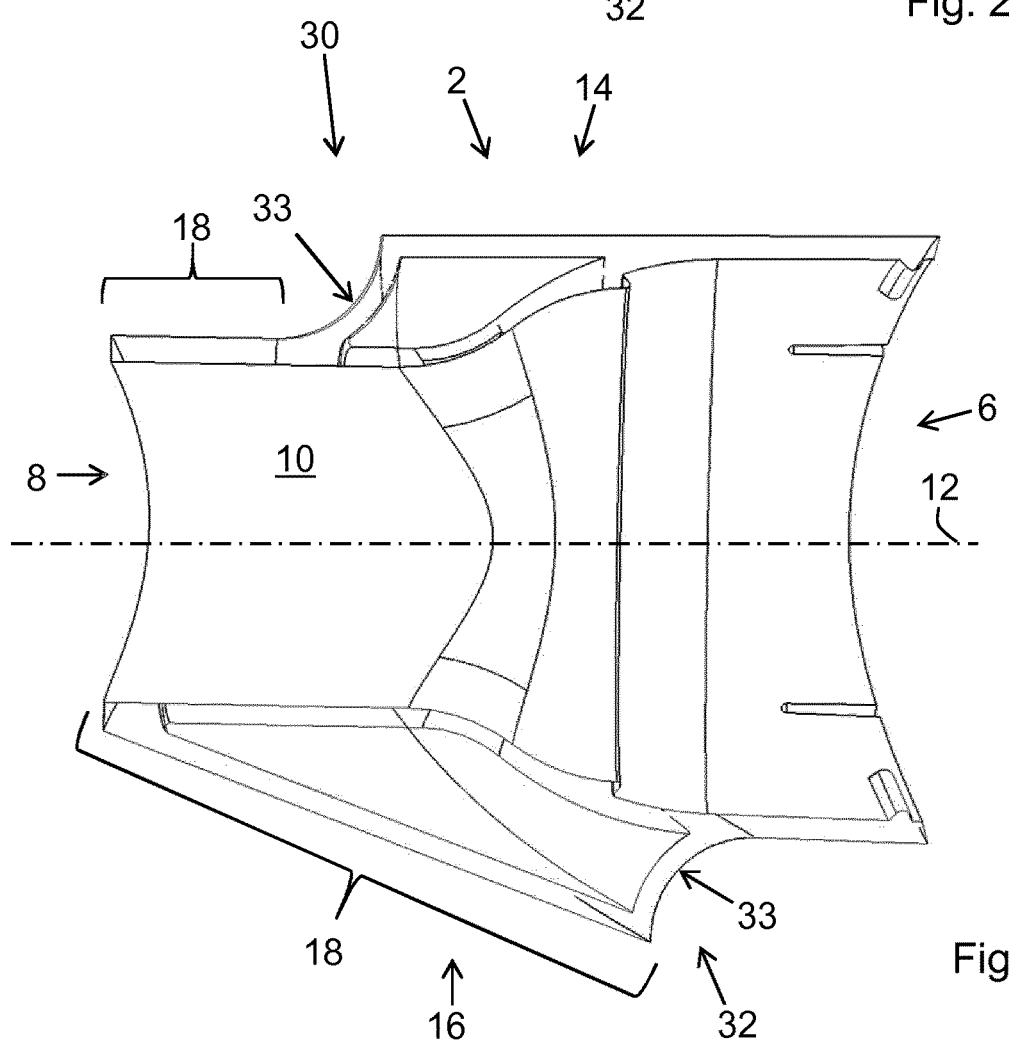

FIGS. 2a and 2b illustrate embodiments of a mouthpiece 2 for use with a handheld inhaler. The mouthpiece 2 forms a part of the inhaler, which is arranged to conduct an aerosol from a medicament container of the inhaler into an oral cavity of a patient. Some features are common with the embodiments of FIGS. 1a and 1b.

Thus again, the mouthpiece 2 comprises a housing 4. The housing 4 comprises an inlet 6 and an outlet opening 8. A channel 10 extends through the housing 4 and connects the inlet 6 and the outlet opening 8. A plane 12 extends through and along the channel 10. The plane 12 defines on respective sides thereof an upper side 14 and a lower side 16 of the housing 4. When the mouthpiece 2 is positioned to be placed in the mouth of the patient, the upper side 14 is arranged to face substantially upwardly and the lower side 16 is arranged to face substantially downwardly. An anterior portion 18 of the housing 4 is adapted to be placed in the mouth of the patient. The anterior portion 18 of the housing 4 is configured to direct the outlet opening 8 upwardly in the oral cavity when the anterior portion is placed in the mouth of the patient.

In these embodiments, groove portions 30, 32 extend at least partially around the housing 4 adjacent to the anterior portion 18. The groove portion 30, 32 are adapted for placing lips of the patient there against. At least one groove portion 30 on the upper side 14 of the housing 4 extends closer to the outlet opening 8 than at least one groove portion 32 on the lower side 16 of the housing 4. The groove portions 30, 32 comprise concavely curved bottom surfaces 33.

When the patient places his or her lips in the groove portions 30, 32 on the upper side 14 and on the lower side 16, the anterior portion 18 will be placed in the mouth of the patient with the plane 12 upwardly inclined to direct the outlet opening 8 upwardly in the oral cavity. The plane 12 may be placed at an angle of 30-60 degrees with a vertical axis. The groove portions 30, 42 may extend across the plane 12 at an angle α of approximately 30-45 degrees. Thus, the anterior portion 18 is longer on the lower side 16 than on the upper side 14.

The following dimensions are mentioned purely as an example. The mouthpiece 2 may have a length of 20-50 mm. The length of the anterior portion 18 may be 10-20 mm at the upper side 14 and 20-40 mm at the lower side 16. The diameter of the outlet opening 8 may be 14-24 mm. The radius of the concavely curved bottom surfaces 33 of the groove portions 30, 32 may be 5-10 mm.

Figure 3A:
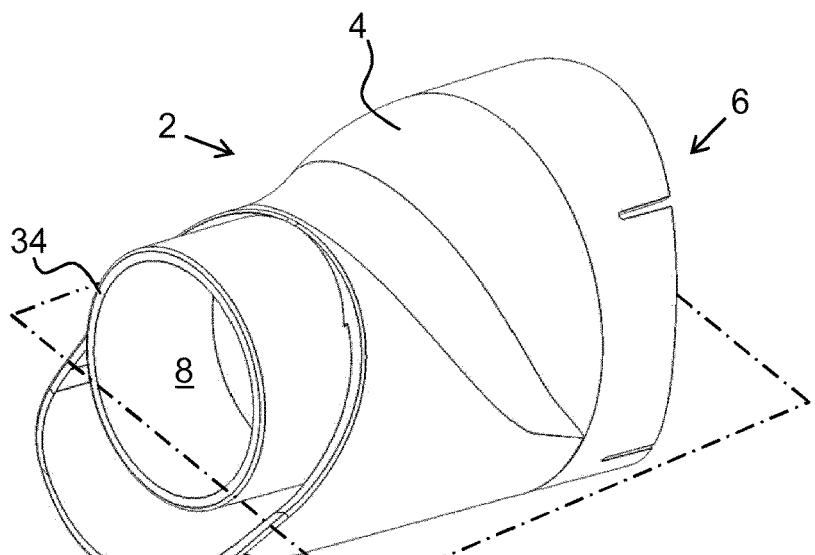
Figure 3B:
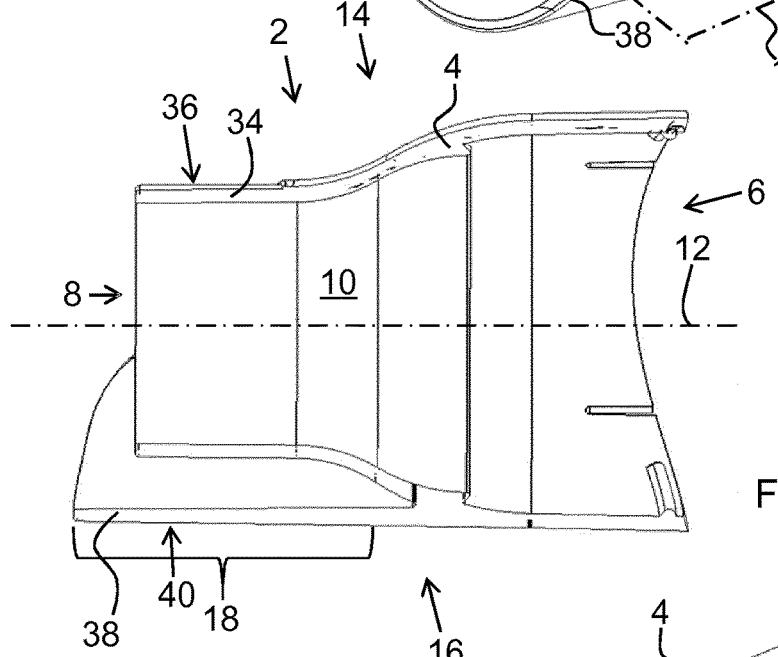

FIGS. 3a and 3b illustrate embodiments of a mouthpiece 2 for use with a handheld inhaler. The mouthpiece 2 forms a part of the inhaler, which is arranged to conduct an aerosol from a medicament container of the inhaler into an oral cavity of a patient. Some features are common with the embodiments of FIGS. 1a-2b.

Thus again, the mouthpiece 2 comprises a housing 4. The housing 4 comprises an inlet 6 and an outlet opening 8. A channel 10 extends through the housing 4 and connects the inlet 6 and the outlet opening 8. A plane 12 extends through and along the channel 10. The plane 12 defines on respective sides thereof an upper side 14 and a lower side 16 of the housing 4. When the mouthpiece 2 is positioned to be placed in the mouth of the patient, the upper side 14 is arranged to face substantially upwardly and the lower side 16 is arranged to face substantially downwardly. An anterior portion 18 of the housing 4 is adapted to be placed in the mouth of the patient.

In these embodiments, the outlet 8 opening is placed closer to the upper side 14 of the housing 4 than to the lower side 16 of the housing 4. Thus, an aerosol from the inhaler being directed into the mouth of the patient from the outlet opening 8 of the mouthpiece 2 is directed over the tongue into the oral cavity to improve the administering of the aerosol from the inhaler to the lungs of the patient.

A channel-forming wall element 34 of the channel 10 forms at least a portion of an upper surface 36 of the anterior portion 18 on the upper side 14 of the housing 4. A distance element 38 is positioned at a distance from the channel 10 and forms at least a portion of a lower surface 40 of the anterior portion 18 on the lower side 16 of the housing 4. Accordingly, the outlet opening 8 is placed closer to the upper side 14 of the housing 4 than to the lower side 16 of the housing 4 to create a distance between the tongue of the patient and the outlet opening 8.

The distance element 38 extends outside the outlet opening 8 seen along the plane 12. The distance element 38 connects to the channel-forming wall element 34 at a middle portion of the channel 10.

The following dimensions are mentioned purely as an example. The mouthpiece 2 may have a length of 10-70 mm. The length of the anterior portion 18 may be 10-40 mm. The diameter of the outlet opening 8 may be 14-24 mm. The distance between the centre of the channel 10, i.e. the plane 12, to the lower surface 40 may be 10-20 mm.

Figure 4:
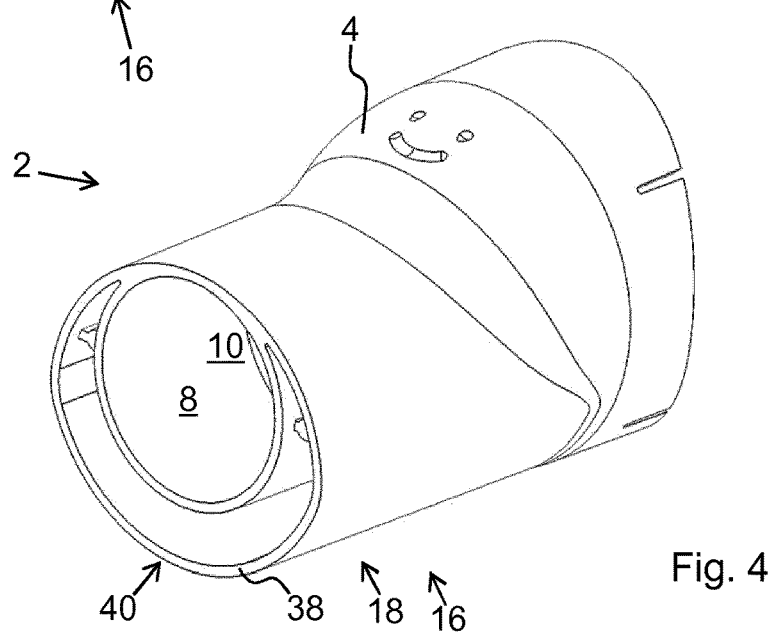

FIG. 4 illustrates embodiments of a mouthpiece 2 for use with a handheld inhaler. The mouthpiece 2 forms a part of the inhaler, which is arranged to conduct an aerosol from a medicament container of the inhaler into an oral cavity of a patient. The mouthpiece 2 according to these embodiments is similar to the mouthpiece according to the embodiments of FIGS. 3a-3b. The main difference lies in that the distance element 38 is shaped differently to create an oval shaped end of the anterior portion 18 at the outlet opening 8. The distance element 38 does not extend beyond the outlet opening 8. However again, the distance element 38 is positioned a distance from the channel 10 and forms at least a portion of a lower surface 40 of the anterior portion 18 on the lower side 16 of the housing 4.

Figure 5:
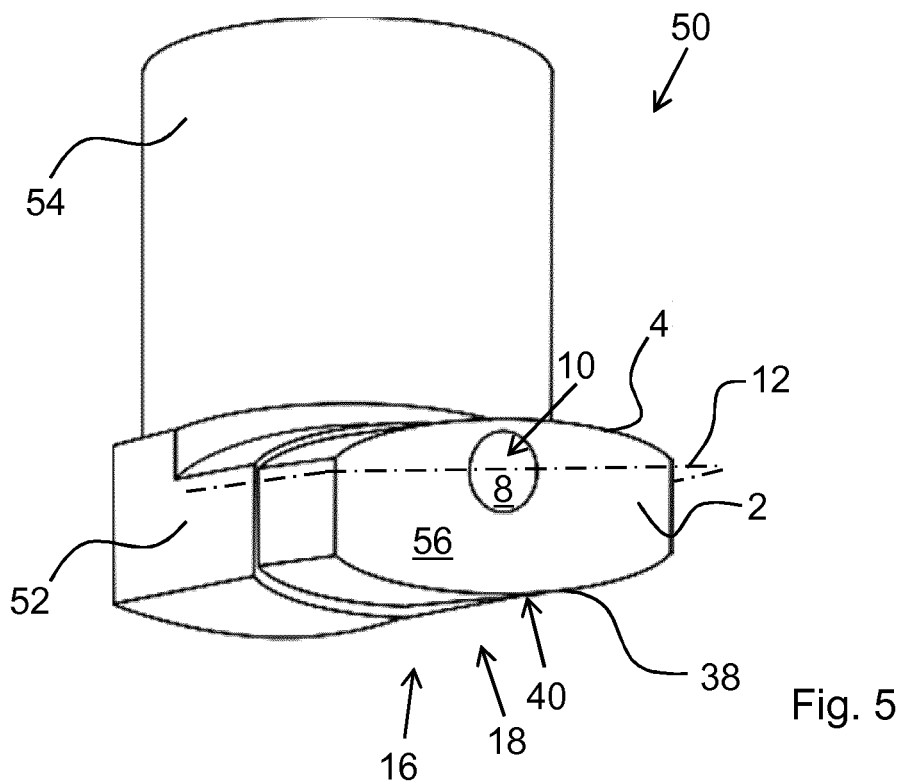
FIGS. 5 and 6 illustrate handheld inhalers according to embodiments.

FIG. 5 illustrates a handheld inhaler 50 according to embodiments. The inhaler 50 comprises a mouthpiece 2, an inhaler body 52, and a medicament container holder 54. The inhaler body 52 and the medicament container holder 54 may form a medicament delivery device. A patient uses the inhaler 50 by placing an anterior portion 18 of the mouthpiece 2 into his or her mouth, and pressing the medicament container holder 54 towards the inhaler body 52 while inhaling to eject a dose of medicament in aerosol form to be administered via the mouthpiece 2 into the mouth and the lungs of the patient.

The mouthpiece 2 according to these embodiments is similar to the mouthpiece according to the embodiments of FIGS. 3a, 3b, and 4. The main difference lies in that the mouthpiece 2 comprises a front surface 56 extending substantially perpendicularly to the plane 12. The outlet opening 8 is arranged in the front surface 56. Again, a distance element 38 is positioned at a distance from the channel 10 forming at least a portion of a lower surface 40 of the anterior portion 18 on the lower side 16 of the housing 4 of the mouthpiece 2.

Figure 6:
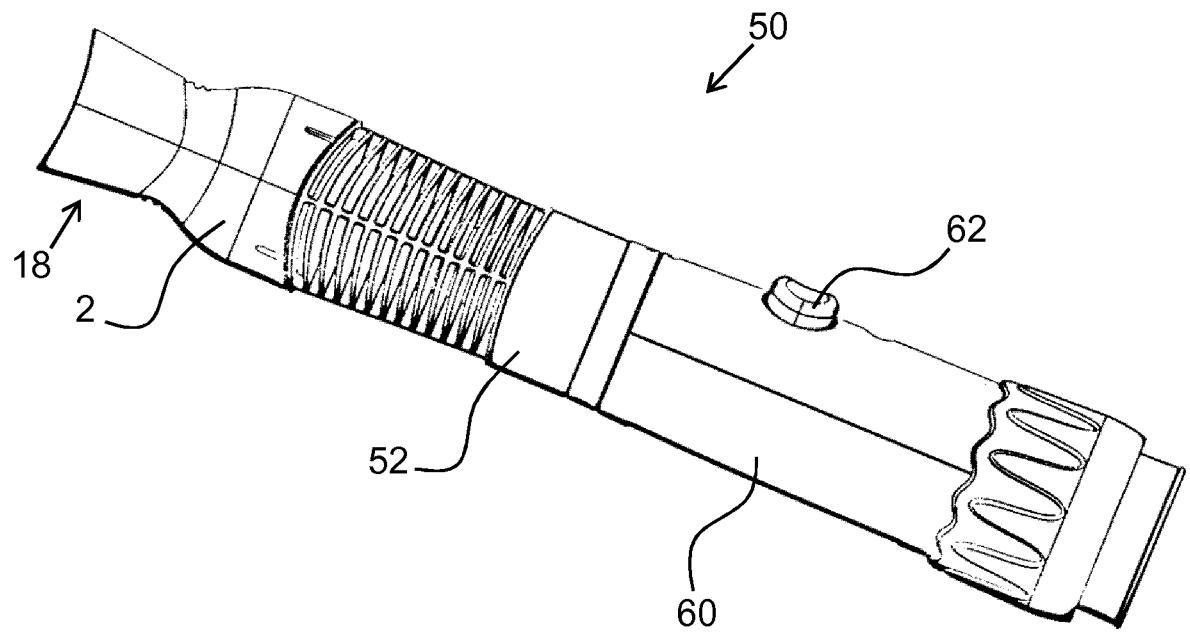

FIG. 6 illustrates a handheld inhaler 50 according to embodiments. The inhaler 50 comprises a mouthpiece 2, an inhaler body 52, inside which a medicament container is arranged, and an energy supplying arrangement 60. The inhaler body 52 and the energy supplying arrangement 60 may form a medicament delivery device. The energy supplying arrangement 60 is loaded by a patient prior to administering an aerosol from the inhaler 50. The patient places an anterior portion 18 of the mouthpiece 2 into his or her mouth, and releases the energy supplying arrangement 60 by pressing the release button 62. At the same time the patient inhales. Thus, a dose of medicament in aerosol form is ejected from the medicament container by the energy supplying arrangement 60 and administered via the mouthpiece 2 into the mouth and the lungs of the patient. The energy supplying arrangement 60 may be reusable. The inhaler body 52 and the mouthpiece 2 may be disposable.

The mouthpiece 2 illustrated in FIG. 6 corresponds to the embodiments illustrated in FIGS. 1a and 1b. Mouthpieces 2 according to other embodiments disclosed herein may alternatively be used.

Similarly, mouthpieces 2 according to embodiments disclosed in FIGS. 1a-4 may alternatively be used in the inhaler 50 according to the embodiments disclosed in FIG. 5.

This invention should not be construed as limited to the embodiments set forth herein. A person skilled in the art will realize that different features of the described embodiments may be combined to create embodiments other than those described herein, without departing from the scope of protection, as defined by the appended claims. The mouthpieces 2 disclosed herein may be manufactured from plastic material, such as polymers. Although the invention has been described with reference to example embodiments, many different alterations, modifications and the like will become apparent for those skilled in the art. Therefore, it is to be understood that the foregoing is illustrative of various example embodiments and that the invention is defined only the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A mouthpiece for a handheld inhaler, comprising:
 a housing comprising,
 an anterior end face comprising a frusto-conical portion having an outside surface and an interior surface that surrounds an outlet opening of a channel located inside of the housing, where the frusto-conical portion and the outlet opening form concentric openings in the anterior end face;
 a posterior end face that defines an inlet opening of the channel, where the posterior end face has an inside surface located circumferentially around a terminal end of the inlet opening, where the inside surface comprises a connector that is configured for attachment to an anterior outlet opening of an aerosol delivery device such the inlet opening and the anterior outlet opening are aligned and directly connected to each other; and
 an outside surface connecting the anterior end face with the posterior end face and having a top positioned between the posterior end face and the anterior end face;
 wherein the channel is in fluid communication and connects the inlet opening with the outlet opening, where the inlet opening and the outlet concentric openings are the only openings in the channel,
 wherein the housing has an upper side and a lower side located on respective sides of a plane extending through and along the channel, where the plane bisects the inlet opening and the outlet opening, and bisects the anterior outlet opening of the aerosol delivery device when connected to the connector,
 wherein the top is located at a distance from and measured perpendicular to the plane, where the top distance is less than perpendicular distances measured at the posterior end face to the plane and the anterior end face to the plane,
 wherein a perpendicular distance measured from an inside wall of the channel at the anterior end face is less than a perpendicular distance measured from the inside wall of the channel at the posterior end face and less than the top distance, and
 wherein the housing has an anterior portion adapted to be placed in a mouth of a patient and configured to direct the outlet opening upwardly in the patient's oral cavity when the anterior portion is placed in the patient's mouth.

2. The mouthpiece of claim 1 where the posterior end face is larger than the anterior end face.

3. The mouthpiece of claim 1, wherein the connector comprises a snap-fit.

4. The mouthpiece of claim 1 further comprising indentations or protrusions located on the outside surface that are configured to provide an indication to the patient that the anterior portion of the housing has been placed within the patient's mouth.

5. A mouthpiece for a handheld inhaler, comprising:
 a housing comprising,
 an anterior end face;

a posterior end face, where the posterior end face has a connector configured for attachment to an aerosol delivery device; and an outside surface connecting the anterior end face with the posterior end face and having a groove positioned between the posterior end face and the anterior end face;

a channel positioned within the housing having an inlet and an outlet, wherein the housing has an upper side and a lower side located on respective sides of a plane extending through and along the channel, wherein the groove is positioned on the upper side and the lower side, wherein the groove on the upper side is located at a distance from and measured perpendicular to the plane such that the upper side groove distance is less than a perpendicular distance measured at the posterior end face to the plane and greater than a perpendicular distance measured at the anterior end face;

wherein the groove on the lower side is located at a distance from and measured perpendicular to the plane such that the lower side groove distance is greater than perpendicular distances measured at the posterior end face to the plane and the anterior end face to the plane;

the housing has an anterior portion adapted to be placed in a mouth of a patient such that the patient's lips are positioned in the groove to direct the outlet upwardly in the patient's oral cavity when the anterior portion is placed in the patient's mouth.

6. The mouthpiece of claim 5 where the groove in the upper side is located closer to the anterior end face than the groove in the lower side.

7. The mouthpiece of claim 6 where the groove is continuous around the outside surface of the housing forming less than a perpendicular angle with respect to the plane.

8. The mouthpiece of claim 5 where the anterior portion on the upper side is generally parallel to the plane and the anterior portion on the lower side is angled away from the plane.

9. The mouthpiece of claim 5 where the posterior end face is larger than the anterior end face.

10. The mouthpiece of claim 5 where the inlet defines an opening in the channel larger that an opening in the outlet.

11. A mouthpiece for a handheld inhaler, comprising:

a housing comprising, an anterior end face;

a posterior end face, where the posterior end face has a connector configured for attachment to an aerosol delivery device; and an outside surface connecting the anterior end face with the posterior end face and having a top positioned between the posterior end face and the anterior end face;

a channel positioned within the housing having a single inlet located at the posterior end face and a single outlet located at the anterior end face, where the channel has an outer wall and directs aerosol from the aerosol delivery device from the inlet to the outlet, wherein the housing has an upper side and a lower side located on respective sides of a plane extending through and along the channel, where the lower side of the housing extends further anteriorly than the upper side of the housing to define a distance element, where the distance element is positioned a distance below the outer wall of the channel at the anterior end face, the distance defines a space between the distance element and the outer wall, wherein the top is located at a distance from and measured perpendicular to the plane, where the top distance is less than a perpendicular distance measured at the posterior end face to the plane;

the housing has an anterior portion adapted to be placed in a mouth of a patient such that the patient's bottom lip engages the distance element to direct the outlet upwardly in the patient's oral cavity when the anterior portion is placed in the patient's mouth.

12. The mouthpiece of claim 11 where the distance element forms a cantilever surface extending below and beyond the channel outlet, where the distance element is located a perpendicular distance from the plane equal to the perpendicular distance measured at the posterior end face to the plane.

13. The mouthpiece of claim 11 where the posterior end face is larger than the anterior end face.

14. The mouthpiece of claim 11 where the inlet defines an opening in the channel larger that an opening in the outlet.

* * * * *